US008822749B2

(12) United States Patent
Van Westrenen et al.

(10) Patent No.: US 8,822,749 B2
(45) Date of Patent: *Sep. 2, 2014

(54) PROCESS FOR THE PREPARATION OF AN OLEFINIC PRODUCT

(75) Inventors: Jeroen Van Westrenen, Amsterdam (NL); Leslie Andrew Chewter, Amsterdam (NL); Ferry Winter, Amsterdam (NL)

(73) Assignee: Shell Oil Company, Houston, TX (US)

( * ) Notice: Subject to any disclaimer, the term of this patent is extended or adjusted under 35 U.S.C. 154(b) by 507 days.

This patent is subject to a terminal disclaimer.

(21) Appl. No.: 12/743,265

(22) PCT Filed: Nov. 19, 2008

(86) PCT No.: PCT/EP2008/065874
§ 371 (c)(1),
(2), (4) Date: Aug. 6, 2010

(87) PCT Pub. No.: WO2009/065876
PCT Pub. Date: May 28, 2009

(65) Prior Publication Data
US 2010/0305375 A1 Dec. 2, 2010

(30) Foreign Application Priority Data

Nov. 19, 2007 (EP) .................................. 07120962
Nov. 19, 2007 (EP) .................................. 07120963
Nov. 19, 2007 (EP) .................................. 07121003
Nov. 19, 2007 (EP) .................................. 07121005
Nov. 19, 2007 (EP) .................................. 07121008
Nov. 19, 2007 (EP) .................................. 07121014

(51) Int. Cl.
| C07C 1/20 | (2006.01) |
| C07C 4/02 | (2006.01) |
| C07C 2/86 | (2006.01) |
| B01J 29/70 | (2006.01) |
| B01J 29/40 | (2006.01) |
| B01J 29/06 | (2006.01) |

(52) U.S. Cl.
CPC ... *C07C 1/20* (2013.01); *C07C 4/02* (2013.01); *B01J 29/70* (2013.01); *C07C 2529/80* (2013.01); *C07C 2529/70* (2013.01); *B01J 29/40* (2013.01); *B01J 29/06* (2013.01); *C07C 2/865* (2013.01)
USPC ............................ 585/640; 585/638; 585/639

(58) Field of Classification Search
CPC ......... C07C 1/20; C07C 2529/80; B01J 29/80
USPC .................. 585/310, 315, 634, 638, 639, 640; 502/67
See application file for complete search history.

(56) References Cited

U.S. PATENT DOCUMENTS

| 1,351,424 | A | | 8/1920 | Jenkins |
| 4,025,575 | A | * | 5/1977 | Chang et al. ................... 585/640 |
| 4,076,796 | A | | 2/1978 | Reh et al. ........................ 423/659 |
| 4,076,842 | A | * | 2/1978 | Plank et al. .................... 423/704 |
| 4,083,889 | A | * | 4/1978 | Caesar et al. ................... 585/640 |
| 4,197,185 | A | | 4/1980 | Le Page et al. .................. 208/71 |
| 4,393,265 | A | * | 7/1983 | Bonifaz .......................... 585/639 |
| 4,397,827 | A | | 8/1983 | Chu ................................ 423/326 |
| 4,544,792 | A | | 10/1985 | Smith et al. .................... 545/533 |
| 4,556,477 | A | | 12/1985 | Dwyer ........................... 208/111 |
| 4,590,320 | A | | 5/1986 | Sapre ............................. 585/324 |
| 4,626,415 | A | | 12/1986 | Tabak ............................ 422/190 |
| 4,665,249 | A | | 5/1987 | Mao et al. ...................... 585/408 |
| 4,684,757 | A | | 8/1987 | Avidan et al. .................. 585/331 |
| 5,037,511 | A | | 8/1991 | Dornhagen et al. ............ 203/37 |
| 5,210,364 | A | * | 5/1993 | Barri et al. ..................... 585/640 |
| 5,254,767 | A | * | 10/1993 | Dwyer ........................... 585/469 |
| 5,367,100 | A | | 11/1994 | Gongwei et al. ............... 585/640 |
| 5,602,289 | A | * | 2/1997 | van Dijk ........................ 585/315 |
| 5,817,906 | A | | 10/1998 | Marker et al. .................. 585/640 |
| 6,046,372 | A | | 4/2000 | Brown et al. ................... 585/640 |
| 6,307,117 | B1 | | 10/2001 | Tsunoda et al. ................ 585/651 |
| 6,339,181 | B1 | | 1/2002 | Chen et al. ..................... 585/653 |
| 6,372,949 | B1 | | 4/2002 | Brown et al. ................... 585/639 |
| 6,517,807 | B2 | | 2/2003 | Verduijn et al. ............... 423/709 |

(Continued)

FOREIGN PATENT DOCUMENTS

| DE | 10027159 | 12/2001 | ................ C07C 1/20 |
| DE | 10043644 | 3/2002 | ............ C07C 29/128 |

(Continued)

OTHER PUBLICATIONS

Baerlocher et al (Atlas of Zeolite Framework Types, Fifth Revised Edition, Elsevier, 2001, p. 9-16).*

(Continued)

*Primary Examiner* — In Suk Bullock
*Assistant Examiner* — Bradley Etherton

(57) ABSTRACT

Process for the preparation of an olefinic product, which process comprises reacting an oxygenate feedstock and an olefinic co-feed in a reactor in the presence of an oxygenate conversion catalyst comprising a molecular sieve having one-dimensional 10-membered ring channels, and a further molecular sieve having more-dimensional channels, wherein the weight ratio between the one-dimensional molecular sieve and the further molecular sieve is in the range of from 1:1 to 100:1, to prepare an olefinic reaction effluent; separating the olefinic reaction effluent into at least a first olefinic fraction and a second olefinic fraction; recycling at least part of the second olefinic fraction; and recovering at least part of the first olefinic fraction as olefinic product.

14 Claims, No Drawings

(56) References Cited

U.S. PATENT DOCUMENTS

| | | | |
|---|---|---|---|
| 6,656,345 B1 | 12/2003 | Chen et al. | 208/113 |
| 6,791,002 B1 | 9/2004 | Abrevaya et al. | 585/648 |
| 6,797,851 B2 | 9/2004 | Martens et al. | 585/640 |
| 6,858,129 B2 | 2/2005 | Mohr et al. | 208/120.01 |
| 6,951,968 B1 | 10/2005 | Dath et al. | 585/653 |
| 6,977,321 B1 | 12/2005 | Dath et al. | 585/653 |
| 7,112,307 B2 | 9/2006 | Abrevaya et al. | 422/142 |
| 7,314,964 B2 | 1/2008 | Abrevaya et al. | 585/651 |
| 2002/0063082 A1 | 5/2002 | Touvelle et al. | 208/134 |
| 2002/0115898 A1 | 8/2002 | Searle | 585/639 |
| 2003/0078463 A1* | 4/2003 | Martens et al. | 585/638 |
| 2003/0125598 A1 | 7/2003 | Chisholm et al. | 585/640 |
| 2003/0181777 A1 | 9/2003 | Powers et al. | 585/648 |
| 2004/0015028 A1 | 1/2004 | Brown et al. | 585/520 |
| 2004/0102667 A1 | 5/2004 | Vora et al. | 585/324 |
| 2005/0070422 A1 | 3/2005 | Chen et al. | 502/64 |
| 2005/0130832 A1 | 6/2005 | Abrevaya et al. | 502/4 |
| 2006/0020155 A1 | 1/2006 | Beech et al. | 585/639 |
| 2006/0106270 A1 | 5/2006 | Glover et al. | 585/639 |
| 2006/0135834 A1 | 6/2006 | Xu et al. | 585/639 |
| 2007/0155999 A1 | 7/2007 | Pujado et al. | 585/327 |
| 2007/0203380 A1 | 8/2007 | Vora et al. | 585/638 |
| 2009/0105429 A1 | 4/2009 | Chewter et al. | 526/67 |

FOREIGN PATENT DOCUMENTS

| | | | | |
|---|---|---|---|---|
| EP | 88494 | | 9/1983 | C07C 1/20 |
| EP | 109059 | | 5/1984 | C07C 11/06 |
| EP | 340576 | | 11/1989 | C07C 41/00 |
| EP | 343454 | | 11/1989 | C07C 41/09 |
| EP | 485145 | | 5/1992 | C07C 11/02 |
| EP | 489497 | | 6/1992 | C07C 11/02 |
| EP | 0596256 | | 10/1993 | B01J 4/00 |
| EP | 0788838 | | 8/1997 | C10G 35/095 |
| EP | 0921181 | | 6/1999 | C10G 11/05 |
| GB | 663901 | | 12/1951 | |
| WO | WO9302994 | | 2/1993 | C07C 2/86 |
| WO | WO9522516 | | 8/1995 | C07C 2/12 |
| WO | WO 96/15082 | * | 5/1996 | C07C 1/20 |
| WO | WO9957085 | | 11/1999 | C07C 4/02 |
| WO | WO9957226 | | 11/1999 | C10G 11/05 |
| WO | WO0026163 | | 5/2000 | C07C 4/02 |
| WO | WO0123500 | | 4/2001 | C10G 3/00 |
| WO | WO0129152 | | 4/2001 | C10G 3/00 |
| WO | WO0134730 | | 5/2001 | C10G 51/00 |
| WO | WO0162689 | | 8/2001 | C07C 1/20 |
| WO | WO0181280 | | 11/2001 | C07C 11/06 |
| WO | WO0185872 | | 11/2001 | C10G 11/18 |
| WO | WO0190279 | | 11/2001 | C10G 11/18 |
| WO | WO0210098 | | 2/2002 | C07C 1/20 |
| WO | WO03020667 | | 3/2003 | C07C 2/08 |
| WO | WO2004018089 | | 3/2004 | B01J 8/04 |
| WO | WO2004018392 | | 3/2004 | C07C 11/02 |
| WO | WO2004031327 | | 4/2004 | C10G 11/18 |
| WO | WO2004037950 | | 5/2004 | C10G 2/00 |
| WO | WO2004056944 | | 7/2004 | C10G 11/05 |
| WO | WO2005016856 | | 2/2005 | C07C 1/20 |
| WO | WO2005028594 | | 3/2005 | C10G 11/16 |
| WO | WO2006020083 | | 2/2006 | C07C 1/20 |
| WO | WO2007135052 | | 11/2007 | C07C 2/86 |

OTHER PUBLICATIONS

IZA Database of Zeolite Structures, available on-line at www.iza-structure.org/databases, accessed Sep. 26, 2012.*

Meier, et al., "Atlas of Zeolite Structure Types Passage," Atlas of Zeolite Framework Types, 2001, pp. 9-20.

Weissermehl., K., et al: Industrial Organic Chemistry, 3$^{rd}$ Edition, Wiley, 1997, pp. 13-28.

Ch. Baerlocher, et al: Database of Zeolite Structures: http://www.iza-structure.org/databases/—May 4, 2010.

* cited by examiner

PROCESS FOR THE PREPARATION OF AN OLEFINIC PRODUCT

PRIORITY CLAIM

The present application claims priority to European Patent Application 07121005.8 filed 19 Nov. 2007; European Patent Application 07121003.3 filed 19 Nov. 2007; European Patent Application 07121014.0 filed 19 Nov. 2007; European Patent Application 07121008.2 filed 19 Nov. 2007; European Patent Application 07120962.1 filed 19 Nov. 2007 and European Patent Application 07120963.9 filed 19 Nov. 2007.

FIELD OF THE INVENTION

This invention relates to a process for the preparation of an olefinic product, in particular including lower olefins such as ethylene and/or propylene. More in particular this invention relates to a process for the conversion of oxygenates into olefins.

BACKGROUND OF THE INVENTION

Processes for the preparation of olefins from oxygenates are known in the art.

U.S. Pat. No. 6,797,851 describes a process for making ethylene and propylene from an oxygenate feed. The process is conducted in two stages using two different zeolite catalysts, wherein in the first stage oxygenates are converted to a light olefin stream, and wherein in the second stage C4+ olefins produced in the first stage are converted to additional ethylene and propylene. The catalyst used for the first stage is a ZSM-5 containing zeolite catalyst. The second stage catalyst is a 10-membered ring zeolite, and ZSM-22, ZSM-23, ZSM-35, ZSM-48 are mentioned. ZSM-35 is preferred. Various embodiments of reaction systems with first and second stage catalyst in separate reaction zones are discussed. Without disclosing an embodiment, it is generally mentioned that the two catalysts can be mixed.

In the known process, significant amounts of aromatics are produced. Most aromatics are produced in the first stage by the conversion of oxygenate over ZSM-5 zeolite, and once formed, aromatics are unlikely to be converted into olefins in the second stage. In Example 2, obtained with ZSM-5 and ZSM-35 the final product after the second stage contains 11 wt % of aromatics.

A positive influence of aromatics in the conversion of methanol or dimethylether to a product containing C2 to C4 olefins olefins is disclosed in U.S. Pat. No. 6,046,372. In the known process, the conversion takes place by contacting a feed containing methanol and/or dimethylether in the presence of an aromatic compound with a catalyst comprising a porous crystalline material, in particular zeolite ZSM-5. In the examples, which were all conducted with ZSM-5, it had been found that the addition of an aromatic compound to the methanol and/or dimethylether feed increased the selectivity of the conversion reaction towards ethylene.

It is desired to provide a process that allows to maximise production of light olefins from an oxygenate feedstock.

SUMMARY OF THE INVENTION

In accordance with the present invention there is provided a process for the preparation of an olefinic product, which process comprises the steps of
a) reacting an oxygenate feedstock and an olefinic co-feed in a reactor in the presence of an oxygenate conversion catalyst comprising a molecular sieve having one-dimensional 10-membered ring channels, and a further molecular sieve having more-dimensional channels, wherein the weight ratio between the one-dimensional molecular sieve and the further molecular sieve is in the range of from 1:1 to 100:1, to prepare an olefinic reaction effluent;
b) separating the olefinic reaction effluent into at least a first olefinic fraction and a second olefinic fraction;
c) recycling at least part of the second olefinic fraction obtained in step b) to step a) as olefinic co-feed; and
d) recovering at least part of the first olefinic fraction obtained in step b) as olefinic product.

DETAILED DESCRIPTION OF THE INVENTION

The process of the invention allows maximising of olefin production, such as ethylene and/or propylene production, from an oxygenate feedstock comprising e.g. methanol and/or dimethylether. It has been found that a oxygenate conversion catalyst including a majority of a molecular sieve having one-dimensional 10-membered ring channels, and a minority of a further molecular sieve having more-dimensional channels, is particularly effective for this purpose, in particular in the case wherein the reaction mixture comprises an olefinic co-feed in addition to the oxygenate.

The olefinic co-feed is, during normal operation, at least partially obtained by recycling part of the olefinic reaction effluent to the reaction zone in which the oxygenate conversion takes place. Without wishing to be bound by a particular hypothesis or theory, it is currently believed that the reaction is dominated by the majority portion of the molecular sieve having one-dimensional 10-membered ring channels. In such molecular sieve an alcohol or ether oxygenate can be converted to an olefinic product by an initial alkylation step with an olefin from the olefinic co-feed, followed by cracking. The presence of a minority portion of a more-dimensional molecular sieve in the oxygenate conversion catalyst was found to significantly improve stability (slower deactivation during extended runs) and hydrothermal stability. Without wishing to be bound by a particular hypothesis or theory, it is presently believed that this is due to the possibility for converting larger molecules by the more-dimensional molecular sieve, that were produced by the 1-dimensional molecular sieve, and which would otherwise form coke precursors or coke.

Examples of an oxygenate that can be used as feedstock in the present invention include alcohols, such as methanol, ethanol, isopropanol, ethylene glycol, propylene glycol; ketones, such as acetone and methylethylketone; aldehydes, such as formaldehyde, acetaldehyde and propionaldehyde; ethers, such as dimethylether, diethylether, methylethylether, tetrahydrofuran and dioxane; epoxides such as ethylene oxide and propylene oxide; and acids, such as acetic acid, propionic acid, formic acid and butyric acid. Further examples are dialkyl carbonates such as dimethyl carbonate or alkyl esters of carboxylic acids such as methyl formate. Of these examples, alcohols and ethers are preferred.

Examples of preferred oxygenates include alcohols, such as methanol, ethanol, isopropanol, ethylene glycol, propylene glycol; and dialkyl ethers, such as dimethylether, diethylether, methylethylether. Cyclic ethers such as tetrahydrofuran and dioxane, are also suitable.

The oxygenate used in the process according to the invention is preferably an oxygenate which comprises at least one oxygen-bonded alkyl group. The alkyl group preferably is a C1-C4 alkyl group, i.e. comprises 1 to 4 carbon atoms; more preferably the alkyl group comprises 1 or 2 carbon atoms and most preferably one carbon atom. The oxygenate can comprise one or more of such oxygen-bonded C1-C4 alkyl groups. Preferably, the oxygenate comprises one or two oxygen-bonded C1-C4 alkyl groups.

More preferably an oxygenate is used having at least one C1 or C2 alkyl group, still more preferably at least one C1 alkyl group.

Preferably the oxygenate is chosen from the group of alkanols and dialkyl ethers consisting of dimethylether, diethylether, methylethylether, methanol, ethanol and isopropanol, and mixtures thereof.

Most preferably the oxygenate is methanol or dimethylether, or a mixture thereof.

In one embodiment, the oxygenate is obtained as a reaction product of synthesis gas. Synthesis gas can for example be generated from fossil fuels, such as from natural gas or oil, or from the gasification of coal. Suitable processes for this purpose are for example discussed in Industrial Organic Chemistry, Klaus Weissermehl and Hans-Jürgen Arpe, 3rd edition, Wiley, 1997, pages 13-28. This book also describes the manufacture of methanol from synthesis gas on pages 28-30.

In another embodiment the oxygenate is obtained from biomaterials, such as through fermentation. For example by a process as described in DE-A-10043644.

By an olefinic composition or stream, such as an olefinic product, product fraction, fraction, feedstock, co-feed, effluent or the like is understood such a composition or stream comprising one or more olefins, unless specifically indicated otherwise. Other species can be present as well. The olefinic composition or stream can comprise one olefin or a mixture of olefins.

In particular the olefinic co-feed can contain a mixture of olefins. Apart from olefins, the olefinic co-feed may contain other hydrocarbon compounds, such as for example paraffinic (including cycloparaffinic), alkylaromatic, aromatic compounds or a mixture thereof. Preferably the olefinic co-feed comprises an olefinic portion of more than 50 wt %, more preferably more than 60 wt %, still more preferably more than 70 wt %, which olefinic portion consists of olefin(s). The olefinic co-feed can also consist essentially of olefin(s).

Any non-olefinic compounds in the olefinic co-feed are preferably paraffinic, including cycloparaffinic compounds. If the olefinic co-feed contains any non-olefinic hydrocarbon, these are preferably paraffinic compounds. Such paraffinic compounds are preferably present in an amount in the range from 0 to 50 wt %, more preferably in the range from 0 to 40 wt %, still more preferably in the range from 0 to 30 wt %.

Preferably, the olefinic co-feed comprises less than 10 wt % of aromatics, more preferably less than 5 wt %, even more preferably less than 1 wt %. It is preferred that the olefinic co-feed comprises substantially no aromatics.

By an olefin is understood an organic compound containing at least two carbon atoms connected by a double bond. A wide range of olefins can be used. The olefin can be a mono-olefin, having one double bond, or a poly-olefin, having two or more double bonds. Preferably olefins present in the olefinic co-feed are mono-olefins.

The olefin(s) can be a linear, branched or cyclic olefin. Preferably, olefins present in the olefinic co-feed are linear or branched olefins.

Preferred olefins in the olefinic co-feed have in the range from 2 to 12, preferably in the range from 3 to 10, and more preferably in the range from 4 to 8 carbon atoms.

Examples of suitable olefins that may be contained in the olefinic co-feed include 1-butene, 2-butene, iso-butene (2-methyl-1-propene), 1-pentene, 2-pentene, 2-methyl-1-butene, 2-methyl-2-butene, 3-methyl-1-butene, 3-methyl-2-butene, 1-hexene, 2-hexene, 3-hexene, 2-methyl-1-pentene, 2-methyl-2-pentene, 3-methyl-1-pentene, 3-methyl-2-pentene, 4-methyl-1-pentene, 4-methyl-2-pentene, 2,3-dimethyl-1-butene, 2,3-dimethyl-2-butene, 3,3-dimethyl-1-butene, cyclopentene, methylcyclopentene or cyclohexene, heptenes, octenes, nonenes and decenes. The preference for specific olefins in the olefinic co-feed may depend on the purpose of the process. Also light olefins propylene and even ethylene can be recycled. Recycling propylene may be an interesting option for maximising ethylene selectivity of the overall process. In one embodiment of the process according to the invention the recycled part of the second olefinic fraction comprises propylene.

In one embodiment the olefinic co-feed contains olefins having 4 or more carbon atoms (i.e. $C_{4+}$ olefins), such as butenes, pentenes, hexenes and heptenes. Preferably the olefinic portion of the olefinic co-feed comprises at least 70 wt % of butenes and/or pentenes, preferably at least 70 wt % of butenes. More preferably the olefinic fraction of the olefinic co-feed comprises at least 90 wt % of butenes and/or pentenes, most preferably at least 90 wt % of butenes. Butenes as co-feed have been found to be particularly beneficial for high ethylene selectivity. The ethylene selectivity of the process can be increased when the olefinic co-feed comprises less than 10 wt % of C5+ olefins, in particular less than 10 wt % of C5+ olefins and paraffins, more in particular less than 10 wt % of C5+ hydrocarbon species. C5+ denotes hydrocarbons with 5 or more carbon atoms. The olefinic co-feed can in particular comprises less than 5 wt % of C5+ olefins, preferably less than 2 wt % of C5+ olefins, based on total hydrocarbons in the olefinic co-feed. The recycle stream can likewise comprise less than 5 wt % of C5+ olefins, preferably less than 2 wt % of C5+ olefins, based on total hydrocarbons in the recycle stream.

The olefinic co-feed can comprise hydrocarbons, preferably olefins, provided by the recycle of step c) and hydrocarbons, preferably olefins, obtained from some other source. For example part of the olefinic co-feed may be derived from a steam cracker or catalytic cracker, for example a stream comprising butenes, or butenes and butanes.

The olefinic co-feed preferably consists, during normal operation, for at least 50 wt %, more preferably at least 80 wt %, still more preferably from 90 to 100 wt % of such a recycle fraction of the reaction product. In a specifically preferred embodiment the olefinic co-feed consists essentially of a recycle fraction of the reaction product. If that is not the case, part of the olefinic co-feed can originate from an external source, in particular during start-up, when no or insufficient olefinic reaction products are available.

The olefinic co-feed in step a) preferably consists, during normal operation, for at least 50 wt %, more preferably at least 80 wt %, still more preferably from 90 to 100 wt % of the recycled part of the second olefinic fraction from step c). Most preferably the olefinic co-feed consists essentially of the recycled part of the second olefinic fraction obtained in step c).

The preferred molar ratio of oxygenate in the oxygenate feedstock to olefin in the olefinic co-feed depends on the specific oxygenate used and the number of reactive oxygen-bonded alkyl groups therein. Preferably the molar ratio of oxygenate to olefin in the total feed lies in the range of 10:1 to 1:10, more preferably in the range of 5:1 to 1:5 and still more preferably in the range of 3:1 to 1:3.

In a preferred embodiment wherein the oxygenate comprises only one oxygen-bonded methyl group, such as methanol, the molar ratio preferably lies in the range from 5:1 to 1:5 and more preferably in the range of 2.5:1 to 1:2.5.

In another preferred embodiment wherein the oxygenate comprises two oxygen-bonded methyl groups, such as for example dimethylether, the molar ratio preferably lies in the range from 5:2 to 1:10 and more preferably in the range of 2:1 to 1:4. Most preferably the molar ratio in such a case is in the range of 1.5:1 to 1:3.

The expression 'molecular sieve' is used in the description and claims for a material containing small regular pores and/or channels and exhibiting catalytic activity in the conversion of oxygenate to olefin. A molecular sieve having one-dimensional 10-membered ring channels is understood to be a molecular sieve having only 10-membered ring channels in one direction which are not intersected by other 8, 10 or 12-membered ring channels from another direction. The molecular sieve having one-dimensional 10-membered ring channels and/or the more-dimensional molecular sieve can in particular be a zeolite. A zeolite is understood to be an aluminosilicate molecular sieve. Where reference is made in the description and in the claims to a molecular sieve, this can in particular be a zeolite.

Molecular sieve and zeolite types are for example defined in Ch. Baerlocher and L. B. McCusker, Database of Zeolite Structures: http://www.iza-structure.org/databases/, which database was designed and implemented on behalf of the Structure Commission of the International Zeolite Association (IZA-SC), and based on the data of the 4th edition of the Atlas of Zeolite Structure Types (W. M. Meier, D. H. Olson and Ch. Baerlocher).

Preferably, the molecular sieve with one-dimensional 10-membered ring channels is selected from the group of TON-type (for example zeolite ZSM-22), MTT-type (for example zeolite ZSM-23), STF-type (for example SSZ-35), SFF-type (for example SSZ-44), EU-2-type/ZSM-48, and EUO-type (for example zeolite ZSM-50) molecular sieves or mixtures thereof.

MTT-type molecular sieves are more particularly described in e.g. U.S. Pat. No. 4,076,842. For purposes of the present invention, MTT is considered to include its isotypes, e.g., ZSM-23, EU-13, ISI-4 and KZ-1.

TON-type molecular sieves are more particularly described in e.g. U.S. Pat. No. 4,556,477. For purposes of the present invention, TON is considered to include its isotypes, e.g., ZSM-22, Theta-1, ISI-1, KZ-2 and NU-10.

EU-2-type molecular sieves are more particularly described in e.g. U.S. Pat. No. 4,397,827. For purposes of the present invention, EU-2 is considered to include its isotypes, e.g., zeolite ZSM-48.

In a further preferred embodiment a molecular sieve of the MTT-type, such as ZSM-23, or a TON-type, such as ZSM-22, or a mixture thereof is used.

The further molecular sieve having more-dimensional channels is understood to have intersecting channels in at least two directions. Preferably the channels in at least one of the directions are 10-membered ring channels. Preferably the channels in both directions are formed by 10-membered ring-channels. A preferred further molecular sieve is an MFI-type molecular sieve, in particular zeolite ZSM-5.

In one embodiment, molecular sieves (zeolites) in the hydrogen form are used, e.g., HZSM-22, HZSM-23, HZSM-48, HZSM-5. Preferably at least 50% w/w, more preferably at least 90% w/w, still more preferably at least 95% w/w and most preferably 100% of the total amount of molecular sieve used is in the hydrogen form, based on total molecular sieve in the oxygenate conversion catalyst. When the molecular sieves are prepared in the presence of organic cations the molecular sieve may be activated by heating in an inert or oxidative atmosphere to remove organic cations, for example, by heating at a temperature over 500° C. for 1 hour or more. The zeolite is typically obtained in the sodium or potassium form. The hydrogen form can then be obtained by an ion exchange procedure with ammonium salts followed by another heat treatment, for example in an inert or oxidative atmosphere at a temperature over 500° C. for 1 hour or more. The molecular sieves obtained after ion-exchange are also referred to as being in the ammonium form.

Preferably the more-dimensional molecular sieve has a silica-to-alumina ratio (SAR) in the range from 1 to 1000. Preferably the molecular sieve having one-dimensional 10-membered ring channels has a SAR in the range from 10 to 400. The SAR is defined as the molar ratio of $SiO_2/Al_2O_3$ corresponding to the composition of the molecular sieve.

For ZSM-22, a SAR in the range of 40-150 is preferred, in particular in the range of 70-120. Good performance in terms of activity and selectivity has been observed with a SAR of about 100.

For ZSM-23, a SAR in the range of 20-120 is preferred, in particular in the range of 30-80. Good performance in terms of activity and selectivity has been observed with a SAR of about 50.

For ZSM-5, a SAR of 60 or higher is preferred, in particular 80 or higher, more preferably 100 or higher, still more preferably 150 or higher, such as 200 or higher.

In one embodiment the oxygenate conversion catalyst can comprise more than 50 wt %, based on total molecular sieve in the oxygenate conversion catalyst, of the one-dimensional molecular sieve having 10-membered ring channels, and in a further embodiment at least 65 wt %. The presence of a large majority of such molecular sieve strongly determines the predominant reaction pathway.

Suitably the catalyst composition comprises at least 1 wt % of the further molecular sieve, based on the total weight of molecular sieves in the catalyst composition, preferably at least 5 wt %, more preferably at least 8 wt %.

Suitably, the catalyst composition comprises less than 35 wt % of the further molecular sieve, based on the total weight of molecular sieves in the catalyst composition, preferably less than 20 wt %, more preferably less than 18 wt %, still more preferably less than 15 wt %.

The molecular sieve can be used as such or in a formulation, such as in a mixture or combination with a so-called binder material, e.g. silicabinder, aluminabinder, silica-alumina binder, zirconiabinder, and/or a filler material, e.g. kaolin, kaolinit, attapulgite, montmorillonite, bentonite, alumina, silica, titania, and optionally also with an active matrix component. Other components can also be present in the formulation. Typically, molecular sieve content, such as in particular zeolite content, in a formulated catalyst is in the range of from 1 wt % to 50 wt %, preferably 10 to 40 wt %, more preferably 20 to 40 wt %, based on total formulated catalyst.

If one or more molecular sieves are used as such, in particular when no binder, filler, or active matrix material is used, the molecular sieve(s) itself is/are referred to as oxygenate conversion catalyst. In a formulation, the molecular sieve(s) in combination with the other components of the mixture such as binder and/or filler material is/are referred to as oxygenate conversion catalyst.

It is desirable to provide a oxygenate conversion catalyst having good mechanical or crush strength, because in an industrial environment the catalyst is often subjected to rough handling which tends to break down the catalyst into powder-like material. The latter causes problems in the processing, such as attrition of catalyst particles in a riser reactor. Preferably the molecular sieve is therefore incorporated in a binder material. Examples of suitable materials in a formulation include active and inactive materials and synthetic or naturally occurring zeolites as well as inorganic materials such as clays, silica, alumina, aluminosilicate. For present purposes, inactive materials of a low acidity, such as silica, are preferred because they may prevent unwanted side reactions which may take place in case a more acidic material, such as alumina is used.

The process of the present invention can be carried out in a batch, continuous, semi-batch or semi-continuous manner. Preferably the process of the present invention is carried out in a continuous manner.

If the process is carried out in a continuous manner, the process may be started up by using olefins obtained from an external source for the olefinic co-feed in step a). Such olefins may for example be obtained from a steam cracker, a catalytic cracker, alkane dehydrogenation (e.g. propane or butane dehydrogenation). Further, such olefins can be bought from the market.

In a special embodiment the olefins for such start-up are obtained from a previous process that converted oxygenates, with or without olefinic co-feed, to olefins. Such a previous process may have been located at a different location or it may have been carried out at an earlier point in time.

The reactor system used in step a) may include any reactor known to the skilled person and may for example contain a fixed bed, moving bed, fluidized bed, riser reactor and the like. A riser reactor system is preferred, in particular a riser reactor system comprising a plurality of serially arranged riser reactors.

Molecular sieves with one-dimensional 10-membered ring channels such as ZSM-22 or ZSM-23 are typically not able to convert an oxygenate feed to an olefinic product stream with any useful conversion, unless an olefinic co-feed is provided. At start-up of a conversion process, no olefinic product is available from which an olefinic recycle co-feed could be obtained. With the presence of a more-dimensional molecular sieve such as ZSM-5, even in minority compared to the one-dimensional molecular sieve, start up is possible without an olefinic co-feed from an external source. ZSM-5 for example is able to convert an oxygenate to an olefin-containing product, so that a recycle can be established.

Typically the oxygenate conversion catalyst deactivates in the course of the process. Conventional catalyst regeneration techniques can be employed. Catalyst particles can be present in the form of spray dried catalyst particles, spheres, tablets, rings, extrudates, etc. Extruded catalysts can be applied in various shapes, such as, cylinders and trilobes. If desired, spent oxygenate conversion catalyst can be regenerated and recycled to the process of the invention.

Step a) of the process can be carried out over a wide range of temperatures and pressures. Suitably, however, the oxygenate feed and olefinic co-feed are contacted with the oxygenate conversion catalyst at a temperature in the range from 200° C. to 650° C. In a further preferred embodiment the temperature is in the range from 250° C. to 600° C., more preferably in the range from 300° C. to 550° C., most preferably in the range from 450° C. to 550° C. Preferably the reaction in step a) is conducted at a temperature of more than 450° C., preferably at a temperature of 460° C. or higher, in particular of 480° C. or higher, more preferably at a temperature of 490° C. or higher. At higher temperatures a higher activity and ethylene selectivity is observed. One-dimensional zeolites having 10-membered ring channels can be operated under oxygenate conversion conditions at such high temperatures with acceptable deactivation due to coking, contrary to molecular sieves with smaller pores or channels, such as 8-membered ring channels. Temperatures referred to hereinabove represent reaction temperatures, and it will be understood that a reaction temperature can be an average of temperatures of various feed streams and the catalyst in the reaction zone.

In addition to the oxygenate, and the olefinic co-feed, a diluent may be fed into the first riser reactor and/or any subsequent riser reactor. It is preferred to operate without a diluent, or with a minimum amount of diluent, such as less than 200 wt % of diluent based on the total amount of oxygenate feed, in particular less than 100 wt %, more in particular less than 20 wt %. Any diluent known by the skilled person to be suitable for such purpose can be used. Such diluent can for example be a paraffinic compound or mixture of compounds. Preferably, however, the diluent is an inert gas. The diluent can be argon, nitrogen, and/or steam. Of these, steam is the most preferred diluent. For example, the oxygenate feed and optionally olefinic co-feed can be diluted with steam, for example in the range from 0.01 to 10 kg steam per kg oxygenate feed.

In one embodiment small amounts of water are added to step a) in order to improve the stability of the catalyst by reducing coke formation.

In one embodiment the molecular sieve having one-dimensional 10-membered ring channels, and/or the further molecular sieve having more-dimensional channels is subjected to a steam treatment before being used in step a).

In step b) of the process according to the invention the olefinic reaction effluent of step a) is separated (fractionated). At least a first olefinic fraction and a second olefinic fraction, preferably containing $C_4$ olefins, are obtained. The first olefinic fraction typically is a light olefinic fraction comprising ethylene, and the second olefinic fraction is typically a heavier olefinic fraction comprising C4 olefins.

Preferably also a water-rich fraction is obtained. Also a lighter fraction comprising contaminants such as methane, carbon monoxide, and/or carbon dioxide can be obtained and withdrawn from the process, as well as one or more heavy fractions comprising C5+ hydrocarbons, including C5+ olefins. Such heavy fraction can for example be used as gasoline blending component. For example, the first olefinic fraction can comprise at least 50 wt %, preferably at least 80 wt %, of C1-C3 species, the recycled part of the second olefinic fraction can comprise at least 50 wt % of $C_4$ species, a heavier carbonaceous fraction that is withdrawn from the process can comprise at least 50 wt % of $C_5$+ species.

In step c) at least part of the second olefinic fraction, preferably containing $C_4$ olefins, obtained in step b) is recycled to step a) as olefinic co-feed.

Only part of the second olefinic fraction or the complete second olefinic fraction may be recycled to step a).

The skilled artisan knows how to separate a mixture of hydrocarbons into various fractions, and how to work up fractions further for desired properties and composition for further use. The separations can be carried out by any method known to the skilled person in the art to be suitable for this purpose, for example by vapour-liquid separation (e.g. flashing), distillation, extraction, membrane separation or a combination of such methods. Preferably the separations are carried out by means of distillation. It is within the skill of the artisan to determine the correct conditions in a fractionation column to arrive at such a separation. He may choose the correct conditions based on, inter alia, fractionation temperature, pressure, trays, reflux and reboiler ratios. The various fractions referred to herein, in particular the recycled part of the second olefinic fraction, can be obtained by fractionating in various stages, and also by blending streams obtained during the fractionation. Typically, an ethylene- and a propylene-rich stream of predetermined purity such as export quality will be obtained from the process, e.g. from a C2 or C3 splitter, and also a stream rich in C4 comprising C4 olefins and optionally C4 paraffins, such as an overhead stream from a debutaniser column receiving the bottom stream from a depropanizer column at their inlet. For example, an amount of the propylene-rich stream can be added to the C4-rich stream, to form the second olefinic fraction being recycled.

Example 1

In this example, dimethyl ether (DME) and 1-butene were reacted over a MTT-type molecular sieve (ZSM-23, SAR=46) physically mixed with MFI-type molecular sieves (ZSM-5) with SAR of 55, 80 and 280, respectively. By feeding 1-butene as olefinic co-feed a process according to the invention is simulated without a recycle. The weight ratio between MTT and MFI physical mixtures in this example was 80/20 wt/wt, respectively. A sample of zeolite powder was pressed into tablets and the tablets were broken into pieces and sieved. For catalytic testing, the sieve fraction of 40-60 mesh has been used. Prior to reaction, the fresh catalyst in its ammonium-form was treated ex-situ in air at 600° C. for 2 hours.

The reaction was performed using a quartz reactor tube of 3.6 mm internal diameter. The catalyst was heated in argon to the reaction temperature of 525° C. and a mixture consisting of 3 vol % dimethyl ether, 3 vol % 1-butene, 2 vol % steam balanced in argon was passed over the catalyst at atmospheric pressure (1 bar). Gas hourly space velocity was 15000 ml/($g_{cat}$·h), based on total gas flow and the mass of oxygenate conversion catalyst $g_{cat}$. Periodically, the effluent from the reactor was analyzed by gas chromatography (GC) to determine the product composition. The composition has been calculated on a weight basis of all hydrocarbons analyzed.

Tables 1-3 show the resulting product composition for the three oxygenate conversion catalysts, and for various times on stream.

TABLE 1

| Oxygenate conversion catalyst | MTT SAR 46/MFI SAR 55 Weight ratio 80:20 | | |
|---|---|---|---|
| Time on stream (h) | 1 | 26 | 47 |
| DME conversion (%) | 100 | 100 | 99.8 |
| Methane (wt %) | 0.91 | 1.8 | 1.9 |
| Ethylene (wt %) | 27.3 | 11.7 | 3.8 |
| Propylene (wt %) | 38.4 | 39.4 | 20.7 |
| C4 total (wt %) | 13.3 | 20.1 | 19.9 |
| C5 total (wt %) | 5.2 | 11.3 | 28.9 |
| C6-C9 total (wt %) | 4.8 | 7.5 | 20.2 |
| C6-C8 aromatics (wt %) | 10 | 8.3 | 4.4 |
| Ethylene/propylene ratio (wt/wt) | 0.71 | 0.3 | 0.19 |
| % C4 saturates of C4 totals | 42 | n.d. | n.d. |

In Table 1 and further tables, n.d. means not determined; Cn total (n being an integer) figures include all hydrocarbon species having n carbon atoms; and C6-C9 total refers to all hydrocarbons having between 6, 7, 8, or 9 carbon atoms, excluding C6-C8 aromatics.

TABLE 2

| Oxygenate conversion catalyst | MTT SAR 46/MFI SAR 80 Weight ratio 80:20 | | |
|---|---|---|---|
| Time on stream (h) | 1 | 26 | 47 |
| DME conversion (%) | 100 | 100 | 100 |
| Methane (wt %) | 0.42 | 0.81 | 1.0 |
| Ethylene (wt %) | 21.1 | 10.4 | 3.5 |
| Propylene (wt %) | 46.4 | 41.4 | 26.4 |
| C4 total (wt %) | 18.9 | 23.5 | 21.4 |
| C5 total (wt %) | 4.2 | 13.0 | 29.4 |
| C6-C9 total (wt %) | 3.9 | 7.5 | 16.9 |
| C6-C8 aromatics (wt %) | 5.1 | 3.3 | 1.4 |
| Ethylene/propylene ratio (wt/wt) | 0.45 | 0.25 | 0.13 |
| % C4 saturates of C4 totals | 17 | n.d. | n.d. |

TABLE 3

| Oxygenate conversion catalyst | MTT SAR 46/MFI SAR 280 Weight ratio 80:20 | | |
|---|---|---|---|
| Time on stream (h) | 1 | 26 | 47 |
| DME conversion (%) | 100 | 100 | 100 |
| Methane (wt %) | 0.40 | 0.3 | 0.36 |
| Ethylene (wt %) | 19.0 | 9.2 | 6.5 |
| Propylene (wt %) | 47.5 | 42.4 | 39.4 |
| C4 total (wt %) | 24.6 | 28.4 | 28.5 |
| C5 total (wt %) | 3.1 | 12.7 | 17.7 |
| C6-C9 total (wt %) | 3.9 | 5.8 | 6.6 |
| C6-C8 aromatics (wt %) | 1.4 | 1.2 | 0.91 |
| Ethylene/propylene ratio (wt/wt) | 0.40 | 0.22 | 0.17 |
| % C4 saturates of C4 totals | 4.4 | n.d. | n.d. |

The oxygenate conversion was in all cases excellent. Deactivation of the catalyst is observed by changing product composition over extended times on stream. Generally, the ethylene selectivity and the ethylene/propylene ratio decrease with increasing time on stream.

Although these experiments did not include a recycle of a product fraction, such recycle was simulated by feeding butene together with the oxygenate. In applying the process of the invention, a low concentration of paraffins in the reaction effluent, in particular of butane and pentane, more in particular of butane, is preferred. This is because it is difficult to economically separate olefins and paraffins with the same number of carbon atoms, in particular butene and butane, such as by distillation. In a preferred embodiment of the present invention, a butene fraction of the reaction effluent is recycled, and this fraction can contain a large portion or substantially all butane of the reaction effluent. Paraffins, in particular butane, can be regarded as inerts at typical oxygenation conditions over the oxygenate conversion catalysts, therefore a certain level of paraffins (butane) will build up.

With increasing SAR of the ZSM-5 component, a decreasing amount of C4 saturates in the total C4 portion of the reaction effluent is observed. Therefore a SAR above 55 is preferred, in particular of 60 or higher, more in particular of 80 or higher, such as 150 or higher. Also with increasing SAR of the ZSM-5 component the amount of aromatics and of other C5+ hydrocarbons decreases, which is preferred for optimum conversion of oxygenate to lower olefins ethylene and propylene.

Comparative Example 2

Under the same conditions as discussed for Experiment 1, experiments were conducted for an oxygenate conversion catalyst consisting only of MTT molecular sieve (ZSM-23) with SAR=46.
The results for various times on stream are shown in Table 4.

TABLE 4

| Oxygenate conversion catalyst | MTT SAR 46 | | |
|---|---|---|---|
| Time on stream (h) | 1 | 26 | 47 |
| DME conversion (%) | 100 | 99.8 | 82.6 |
| Methane (wt %) | 0.41 | 0.50 | 0.57 |
| Ethylene (wt %) | 21.1 | 5.7 | 0.75 |
| Propylene (wt %) | 48.2 | 37.2 | 5.3 |
| C4 total (wt %) | 22.8 | 20.4 | 14.7 |
| C5 total (wt %) | 2.8 | 30 | 42.2 |
| C6-C9 total (wt %) | 3.9 | 5.2 | 26.2 |
| C6-C8 aromatics (wt %) | 0.71 | 0.87 | 0.14 |
| Ethylene/propylene ratio (wt/wt) | 0.44 | 0.15 | 0.14 |
| % C4 saturates of C4 totals | 4.4 | n.d. | n.d. |

The deactivation of molecular sieve ZSM-23 alone is much faster, as can be seen from the decreased oxygenate conversion at 47 hours. The ethylene yield is initially comparable to that in Examples 1, but decreases with increasing time on stream.

Comparative Example 3

Under the same conditions as discussed for Experiment 1, experiments were conducted for two oxygenate conversion catalysts consisting only of MFI molecular sieve (ZSM-5), with SAR=55 and SAR=280, respectively.
The results are shown in Table 5.

TABLE 5

| Oxygenate conversion catalyst | MFI SAR 55 | MFI SAR 280 |
|---|---|---|
| Time on stream (h) | 1 | 1 |
| DME conversion (%) | 100 | 100 |
| Methane (wt %) | 1.0 | 0.82 |
| Ethylene (wt %) | 24.3 | 11.9 |
| Propylene (wt %) | 35.3 | 43.5 |
| C4 total (wt %) | 19 | 28.5 |
| C5 total (wt %) | 5.7 | 8.5 |
| C6-C9 total (wt %) | 3.4 | 3.6 |
| C6-C8 aromatics (wt %) | 11.3 | 3.2 |
| Ethylene/propylene ratio (wt/wt) | 0.69 | 0.27 |
| % C4 saturates of C4 totals | 47 | 6.4 |

Both MFI zeolites show lower total yield of lower olefins (ethylene+propylene) than the mixtures according to the invention in Example 1. Moreover, larger quantities of by-products are formed, i.e. higher amounts of aromatics and other C5+ hydrocarbon species when comparing experiments with MFI of the same SAR. Also the portion of C4 saturates of total C4 is higher for pure ZSM-5 molecular sieve.

ZSM-5 with SAR=55 produces an undesirably large fraction of C4 saturates (butane). ZSM-5 with SAR=280 exhibits a much lower ethylene selectivity at a run time of 1 hour, compared to the results of Experiment 1.

Example 3

In this example, dimethyl ether (DME) and 1-butene were reacted over a TON-type molecular sieve (ZSM-22, SAR=98) physically mixed with MFI-type molecular sieves with SAR of 55, 80 and 280, respectively. The reactions were conducted as discussed for Experiment 1, with the exception of gas hourly space velocity which was 30000 ml/($g_{cat}$·h).

Tables 6-8 show the resulting product composition for the three oxygenate conversion catalysts, and for various times on stream.

TABLE 6

| Oxygenate conversion catalyst | TON SAR 98/ MFI SAR 55 Weight ratio 80:20 | |
|---|---|---|
| Time on stream (h) | 1 | 15 |
| DME conversion (%) | 100 | 99.1 |
| Methane (wt %) | 0.57 | 1.2 |
| Ethylene (wt %) | 17.4 | 3.1 |
| Propylene (wt %) | 44.3 | 20.5 |
| C4 total (wt %) | 19.9 | 19.0 |
| C5 total (wt %) | 7.1 | 32.8 |
| C6-C9 total (wt %) | 3.1 | 20.7 |
| C6-C8 aromatics (wt %) | 7.5 | 2.0 |
| Ethylene/propylene ratio (wt/wt) | 0.39 | 0.15 |
| % C4 saturates of C4 totals | 27.1 | n.d. |

TABLE 7

| Oxygenate conversion catalyst | TON SAR 98/ MFI SAR 80 Weight ratio 80:20 | |
|---|---|---|
| Time on stream (h) | 1 | 15 |
| DME conversion (%) | 100 | 100 |
| Methane (wt %) | 0.29 | 0.64 |
| Ethylene (wt %) | 15.5 | 6.2 |
| Propylene (wt %) | 46.3 | 37.2 |
| C4 total (wt %) | 24.1 | 24.4 |
| C5 total (wt %) | 4.9 | 19.9 |
| C6-C9 total (wt %) | 5.8 | 8.3 |
| C6-C8 aromatics (wt %) | 3.1 | 3.3 |
| Ethylene/propylene ratio (wt/wt) | 0.34 | 0.17 |
| % C4 saturates of C4 totals | 12.6 | n.d. |

TABLE 8

| Oxygenate conversion catalyst | TON SAR 98/ MFI SAR 280 Weight ratio 80:20 | |
|---|---|---|
| Time on stream (h) | 1 | 15 |
| DME conversion (%) | 100 | 99.7 |
| Methane (wt %) | 0.34 | 0.22 |
| Ethylene (wt %) | 14.0 | 5.4 |
| Propylene (wt %) | 46.7 | 39.0 |
| C4 total (wt %) | 28.9 | 29.1 |
| C5 total (wt %) | 6.7 | 20.6 |
| C6-C9 total (wt %) | 2.5 | 4.2 |
| C6-C8 aromatics (wt %) | 0.9 | 1.3 |
| Ethylene/propylene ratio (wt/wt) | 0.30 | 0.14 |
| % C4 saturates of C4 totals | 4.4 | n.d. |

The results are generally similar to those of Example 1. In all cases, a higher total yield of lower olefins (ethylene+propylene) was achieved than with the MFI molecular sieves of Comparative Example 3. Also less by-products are formed, i.e. lower amounts of aromatics and other C5+ hydrocarbon species when comparing experiments with MFI of the same SAR. Also the portion of C4 saturates of total C4 is lower than with pure ZSM-5 molecular sieve.

With increasing SAR of the ZSM-5 component, a decreasing amount of unwanted by-products is obtained, similar to Example 1.

Comparative Example 4

Under the same conditions as discussed for Experiment 3, experiments were conducted for an oxygenate conversion catalyst consisting only of TON molecular sieve (ZSM-22) with SAR=98.
The results for various times on stream are shown in Table 9.

TABLE 9

| Oxygenate conversion catalyst | TON SAR 98 | |
|---|---|---|
| Time on stream (h) | 1 | 15 |
| DME conversion (%) | 99.8 | 92.4 |
| Methane (wt %) | 0.32 | 0.36 |
| Ethylene (wt %) | 16.2 | 0.86 |
| Propylene (wt %) | 45.8 | 9.9 |
| C4 total (wt %) | 28.5 | 14.8 |
| C5 total (wt %) | 6.0 | 39.6 |
| C6-C9 total (wt %) | 2.5 | 29.3 |
| C6-C8 aromatics (wt %) | 0.66 | 0.41 |
| Ethylene/propylene ratio (wt/wt) | 0.35 | 0.09 |
| % C4 saturates of C4 totals | 1.8 | n.d. |

The deactivation of molecular sieve ZSM-22 alone is faster than with the mixtures of Example 4.

Example 5

In this example, dimethyl ether (DME) and 1-butene were reacted over a MTT-type molecular sieve (ZSM-23, SAR=46) physically mixed with MFI-type molecular sieves with SAR=280, in various weight ratios. The reactions were conducted as discussed for Experiment 1.
Table 10 show the resulting product composition for the three mixtures.

TABLE 10

| Oxygenate conversion catalyst | MTT SAR 46/MFI SAR 280 | | |
|---|---|---|---|
| MTT:MFI (w/w) | 90:10 | 80:20 | 70:30 |
| Time on stream (h) | 1 | 1 | 1 |
| DME conversion (%) | 100 | 100 | 100 |
| Methane (wt %) | 0.31 | 0.40 | 0.34 |
| Ethylene (wt %) | 19.1 | 19.0 | 16.9 |
| Propylene (wt %) | 49.1 | 47.5 | 47.3 |
| C4 total (wt %) | 24.5 | 24.6 | 25.7 |
| C5 total (wt %) | 3.0 | 3.1 | 3.5 |
| C6-C9 total (wt %) | 2.8 | 3.9 | 4.5 |
| C6-C8 aromatics (wt %) | 1.2 | 1.4 | 1.7 |
| Ethylene/propylene ratio (wt/wt) | 0.39 | 0.40 | 0.36 |
| % C4 saturates of C4 totals | 3.4 | 4.4 | 6.0 |

From these experiments it can be concluded that 10 wt % of more-dimensional molecular sieve in the oxygenate conversion catalyst can be sufficient to obtain the advantages of the present invention.

Examples 6

In these examples methanol and 1-butene were reacted over a TON-type zeolite with or without physically mixing it with MFI-type zeolites ZSM-5 with a silica-to-alumina ratio of 280. The weight ratio between TON and MFI physical mixtures in this example was 80:20 wt/wt. A sample of zeolite powder was pressed into tablets and the tablets were broken into pieces and sieved. For catalytic testing, the sieve fraction of 40-60 mesh has been used. Prior to reaction, the fresh catalyst in its ammonium-form was treated ex-situ in air at 600° C. for 2 hours. The pure TON-type zeolite as well as the physical mixture were subjected to a steam treatment prior to evaluation of the catalytic performance. This treatment was performed at 600° C. for 5 h in flowing gas containing 30 vol % steam balanced by argon.

The reactions were performed using a quartz reactor tube of 2 mm internal diameter. The catalyst was heated in nitrogen to the reaction temperature of 525° C., and a mixture consisting of 6 vol % methanol with 3 vol % 1-butene balanced in N2 was passed over the catalyst at atmospheric pressure (1 bar). Gas hourly space velocity was 29000 ml/($g_{cat}$·h), based on total gas flow and the mass of oxygenate conversion catalyst $g_{cat}$.

Tables 11 and 12 show the resulting product composition for the pure TON and TON/MFI mixture catalysts after steam treatment, for various times on stream.

TABLE 11

| Oxygenate conversion catalyst | TON SAR 98, steam treated | |
|---|---|---|
| Time on stream (h) | 1 | 6 |
| DME conversion (%) | 100 | 84 |
| Methane (wt %) | 0 | 0 |
| Ethylene (wt %) | 12.3 | 1.1 |
| Propylene (wt %) | 40.3 | 8.1 |
| C4 total (wt %) | 28 | 20 |
| C5 total (wt %) | 15.9 | 35.5 |
| C6-C9 total (wt %) | 2.3 | 22.4 |
| C6-C8 aromatics (wt %) | 0.32 | 0.07 |
| Ethylene/propylene ratio (wt/wt) | 0.31 | 0.1 |
| % C4 saturates of C4 totals | 2.8 | n.d. |

TABLE 12

| Oxygenate conversion catalyst | TON SAR 98:MFI SAR 280 Weight ratio 80:20, steam treated | |
|---|---|---|
| Time on stream (h) | 1 | 6 |
| DME conversion (%) | 100 | 100 |
| Methane (wt %) | 0.4 | 0.4 |
| Ethylene (wt %) | 10.2 | 4.1 |
| Propylene (wt %) | 42.4 | 33.8 |
| C4 total (wt %) | 27.8 | 27.6 |
| C5 total (wt %) | 13.5 | 24.3 |
| C6-C9 total (wt %) | 4.3 | 8.2 |
| C6-C8 aromatics (wt %) | 0.5 | 0.5 |
| Ethylene/propylene ratio (wt/wt) | 0.24 | 0.12 |
| % C4 saturates of C4 totals | 4.3 | n.d. |

Clearly, the catalyst including 20% of MFI type zeolite shows improved stability after hydrothermal treatment.

Comparable behaviour, after hydrothermal treatment, was also observed in experiments comparing pure MTT zeolite and mixtures of MTT/MFI with SAR 280 (90/10; 80/20; and 70/30 w/w).

What is claimed is:
1. A process for the preparation of an olefinic product, which process comprises the steps of a) reacting an oxygenate feedstock and an olefinic co-feed in a reactor in the presence of an oxygenate conversion catalyst comprising a molecular sieve in the hydrogen form having one-dimensional 10-membered ring channels selected from the group consisting of ZSM-22 having a SAR in the range of 40-150, ZSM-23 having a SAR in the range of 20-120 and mixtures thereof, and a further molecular sieve in the hydrogen form having more-dimensional channels, wherein the weight ratio between the one-dimensional molecular sieve and the further molecular sieve is in the range of from 1:1 to 100:1, to prepare an olefinic reaction effluent comprising ethylene and propylene;

b) separating the olefinic reaction effluent into at least a first olefinic fraction and a second olefinic fraction;

c) recycling at least part of the second olefinic fraction obtained in step b) to step a) as olefinic co-feed; and d) recovering at least part of the first olefinic fraction obtained in step b) as an olefinic product comprising ethylene and/or propylene.

2. A process according to claim 1, wherein the further molecular sieve is a MFI-type molecular sieve.

3. A process according to claim 2, wherein the further molecular sieve is a MFI-type molecular sieve having a Silica-to-Alumina ratio SAR of at least 60.

4. A process according to claim 1, wherein the oxygenate feedstock comprises a compound with at least one oxygen-bonded alkyl group.

5. A process according to claim 1, wherein the second olefinic fraction contains olefins having 4 or more carbon atoms.

6. A process according to claim 1, wherein the olefinic product comprises ethylene and/or propylene.

7. A process according to claim 1, wherein at least 70 wt % of the olefinic co-feed in step a), during normal operation, is formed by the recycle stream of step c.

8. A process according to claim 1, wherein the recycled part of the second olefinic fraction comprises at least 50 wt % of C4 olefins, and at least a total of 70 wt % of C4 hydrocarbon species.

9. A process according to claim 1, wherein the olefinic reaction effluent comprises 10 wt % or less of C6-C8 aromatics, based on total hydrocarbons in the effluent.

10. A process according to claim 1, wherein the olefinic co-feed comprises less than 5 wt % of C5+ olefins, based on total hydrocarbons in the olefinic co-feed.

11. A process according to claim 1, wherein step a) is conducted at a temperature of more than 450° C.

12. A process according to claim 1, wherein step a) is performed in a reactor system comprising two or more serially arranged riser reactor stages to obtain a riser reactor effluent from each stage, wherein each riser reactor stage comprises a single riser reactor or a plurality of parallel riser reactors, such that at least part of the riser reactor effluent of a preceding riser reactor stage is fed into a subsequent riser reactor stage.

13. A process according to claim 1, wherein step a) is performed in a reactor system comprising a plurality of sequential reaction zones, and wherein oxygenate is added to at least two of the sequential reaction zones.

14. A process according to claim 1, wherein the oxygenate is obtained as a reaction product of synthesis gas.

\* \* \* \* \*